United States Patent [19]

Maffei et al.

[11] 4,016,874
[45] Apr. 12, 1977

[54] THREE-PART INTRAMEDULLARY BONE-SETTING PIN

[76] Inventors: Ernest J. Maffei, 1681 James St., Syracuse, N.Y. 13203; David W. Patch, 101 Clareview Drive, Clay, N.Y. 13041

[22] Filed: May 19, 1976

[21] Appl. No.: 688,056

[52] U.S. Cl. .......................................... 128/92 BC
[51] Int. Cl.² ................... A61F 5/04; A61B 17/18
[58] Field of Search ........ 128/92 BC, 92 B, 92 BA, 128/92 BB, 92 G, 92 R, 83

[56] References Cited

UNITED STATES PATENTS

| | | | |
|---|---|---|---|
| 2,490,364 | 12/1949 | Livingston | 128/92 BA |
| 2,672,861 | 3/1954 | Jonas et al. | 128/92 BC |
| 2,675,801 | 4/1954 | Bambara et al. | 128/92 BC |
| 2,985,168 | 5/1961 | Jonas et al. | 128/92 R X |
| 3,717,146 | 2/1973 | Halloran | 128/92 BC |
| 3,744,488 | 7/1973 | Cox | 128/92 BC |

FOREIGN PATENTS OR APPLICATIONS 885,910   8/1953   Germany ................ 128/92 BC

*Primary Examiner*—Ronald L. Frinks
*Attorney, Agent, or Firm*—Bruns & Jenney

[57] ABSTRACT

A pin for insertion in the intramedullary passage of a broken bone has two generally tubular outer parts for insertion into the respective parts of a broken bone from an incision at the break, each having tapping threads along the distal end thereof and following threads along the proximal end thereof. The outer parts each have a reduced central axial hole which is square along a portion of both the distal and proximal ends thereof. The third central major part is a rod substantially equal in length to the combined lengths of the outer parts and having a cross-sectional configuration substantially conforming to the square portion of the axial hole of the tubular parts for a slide fit therethrough. One end of the central part has a recess in one end containing a spring pressed locking ball projecting outwardly from one side thereof and one or both tubular parts have a recess therein adapted for locking engagement with the spring-pressed ball when in register therewith. The central part has a plurality of longitudinally spaced recesses along at least one side whereby the central part may be moved from within one tubular part into the other tubular part when the tubular parts are aligned and spaced apart.

6 Claims, 22 Drawing Figures

U.S. Patent April 12, 1977 4,016,874
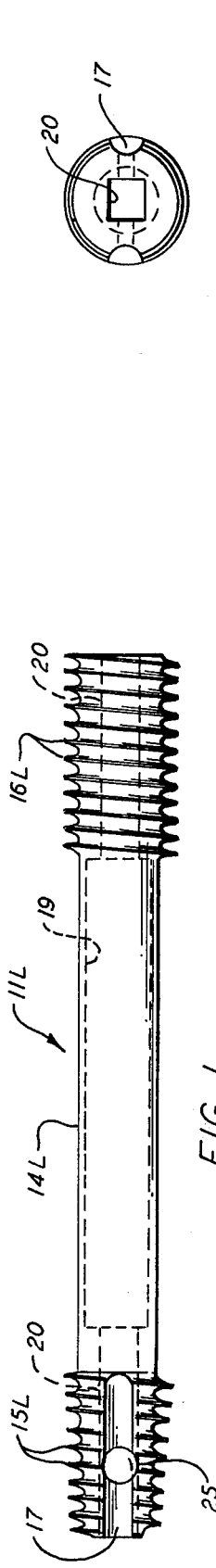
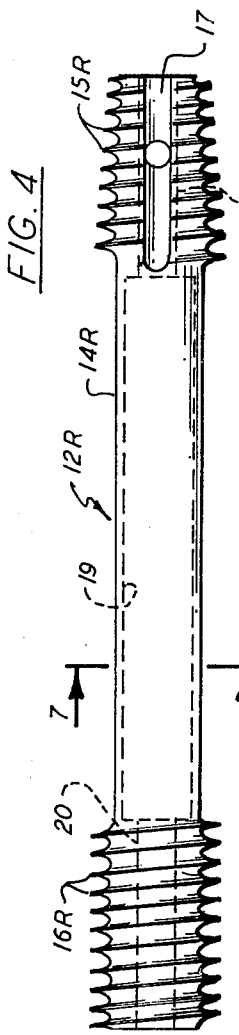
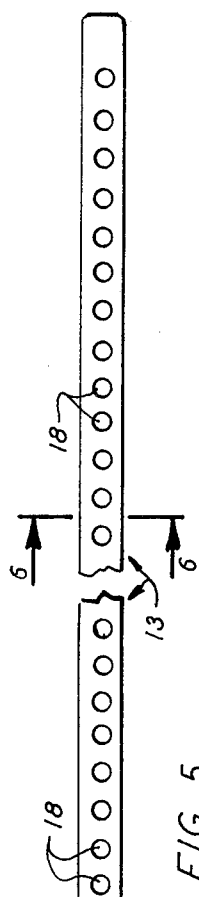
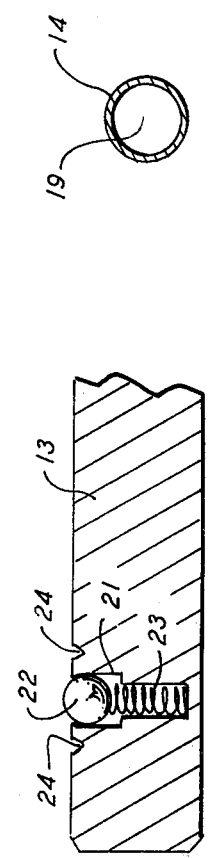
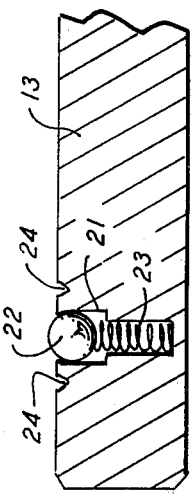
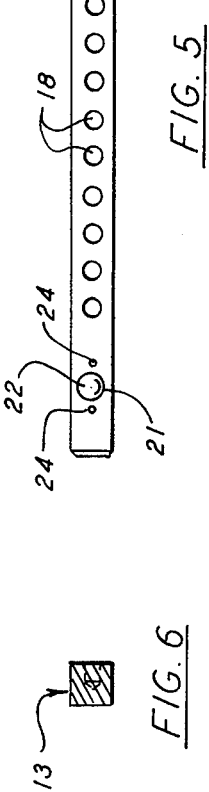

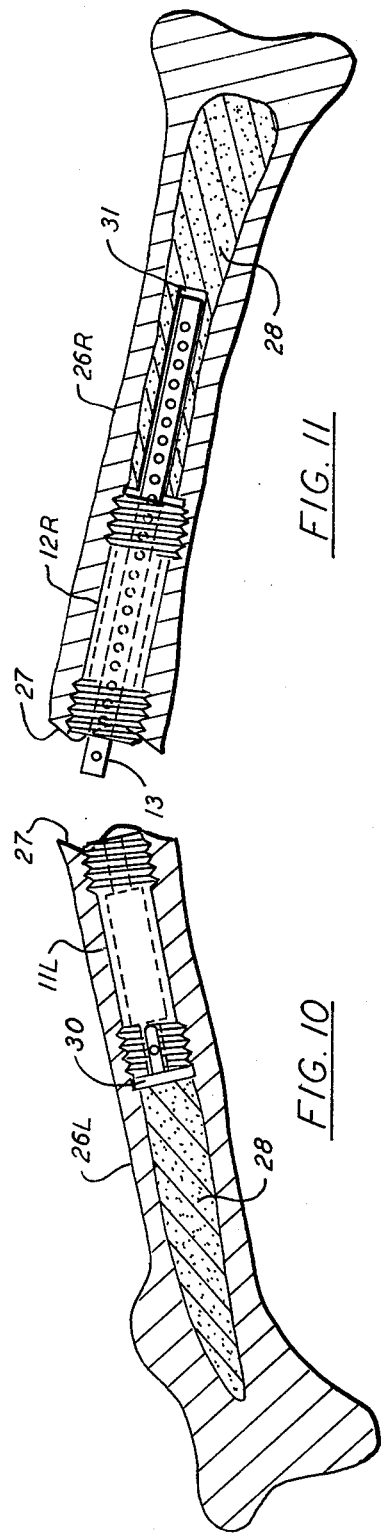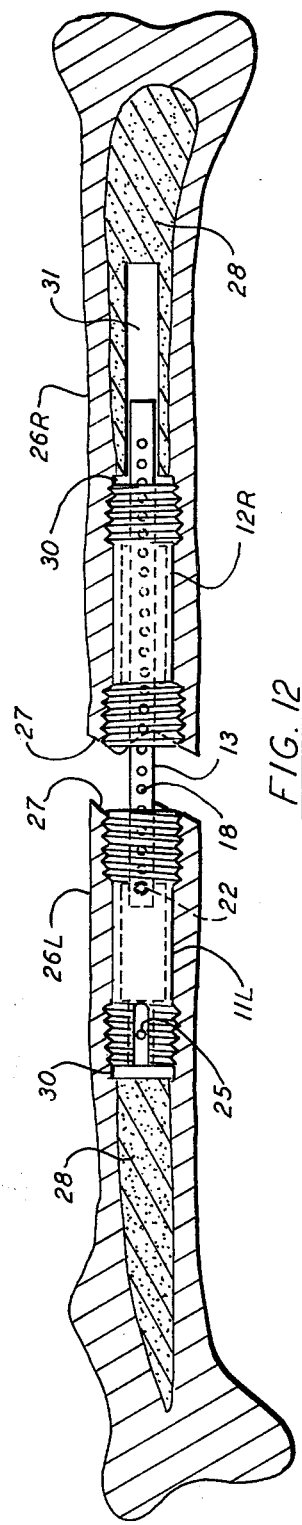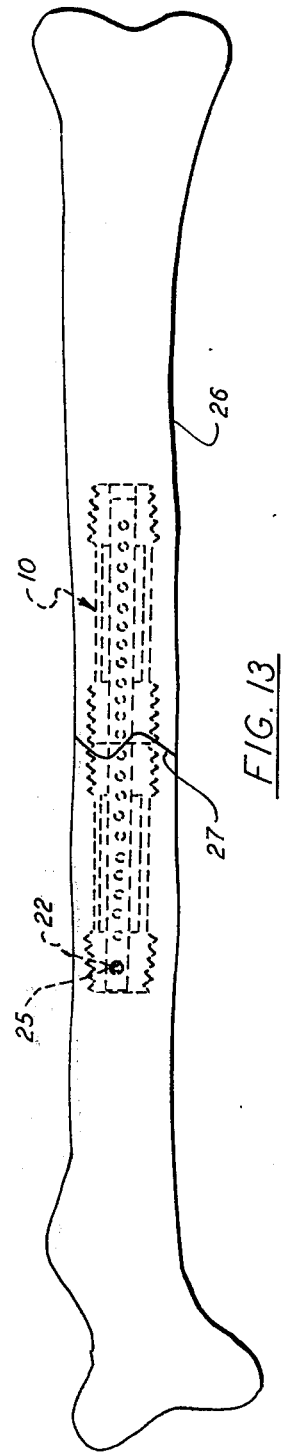

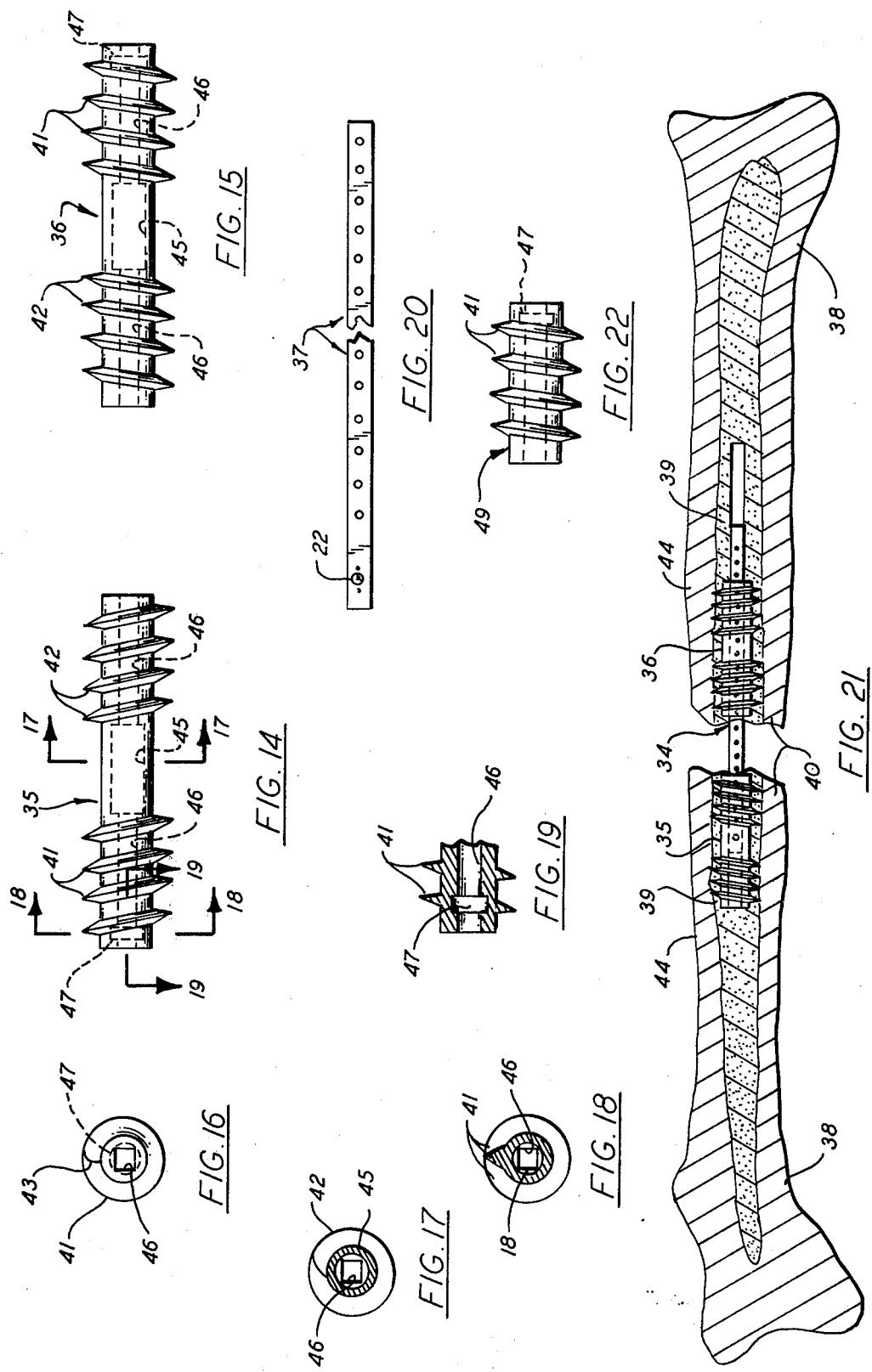

THREE-PART INTRAMEDULLARY BONE-SETTING PIN

BACKGROUND OF THE INVENTION

This invention relates generally to surgical apparatus and more particularly to a bone-setting pin or spline which can be inserted in the intramedullary passage of the two parts of an elongated broken bone, such as an arm or leg bone, through an incision in the limb involved at the break to align the broken parts of the bone and to prevent rotation or torsion of one bone part with respect to the other.

Prior art bone-setting devices either have exterior plate members secured to the bone parts by pins or screws which injure the flesh and muscle surrounding the bone or have similar transversely extending fastening devices through the bone which weaken the hard outer layer of the bone. Other devices must be inserted from one end of the bone and then removed after the fracture has healed. Still other devices keep the parts of the bone on either side of the fracture in alignment but do not prevent rotation of one bone part about the bone axis with respect to the other part. Such devices require immobilizing casts or other restraining means which must be worn for a considerable length of time to prevent torsional movement of the bone parts.

SUMMARY OF THE INVENTION

This invention contemplates a pin or spline of three main parts, two tubular outer members which may be securely anchored in the intramedullary passage of the bone parts on either side of the fracture and firmly secured to the dense outer layer or cortex of the bone halves, and a central rod of irregular cross-sectional shape, most conveniently square, which has a close contact with square, axially extending passages in the outer members for holding the outer members in alignment and for preventing one outer member from rotation with respect to the other aligned member about the common axis of the rod and the aligned outer members.

It is contemplated that the three parts may be inserted into the intramedullary passage from a single incision, typically 4 inches long, located at the point of the break. Each bone half or portion on either side of the break has a respective one of the outer members inserted in the intramedullary passage thereof and the central member may then be inserted in one of the outer members and then moved into the other outer member, means being provided on the central member for axially moving it axially into the other outer member by a pick or similar instrument inserted through the incision. Detent means are provided for holding the central member in place when it is in position.

There are no plate or fastening means projecting radially or axially outward from the bone and the parts are made of a body-acceptable material so that they do not later have to be removed.

BRIEF DESCRIPTION OF THE DRAWINGS

FIG. 1 is a side elevational view of one form of the tubular outer members;

FIG. 2 is a side elevational view of the other similar tubular outer member;

FIG. 3 is an end elevational view of the members shown in FIGS. 1 and 2, showing substantially the right end of FIG. 1 and the left end of FIG. 2;

FIG. 4 is an end elevational view showing substantially the opposite ends of FIGS. 1 and 2;

FIG. 5 is a fragmentary side elevational view of the central rod member;

FIG. 6 is a sectional view on the line 6—6 of FIG. 5;

FIG. 7 is a sectional view on the line 7—7 of FIG. 2;

FIG. 8 is a greatly enlarged fragmentary side elevational view of the left end of FIG. 5;

FIG. 9 is a sectional view on the line 9—9 of FIG. 8;

FIGS. 10 and 11 are diagrammatic longitudinal sectional views, reduced in scale, of the portions of an elongated bone on either side of a fracture, the portions of the intramedullary spline of the present invention being shown inserted therein prior to assembly of the spline;

FIG. 12 is a diagrammatic sectional view of the bone shown in FIGS. 10 and 11, the spline of the present invention being shown while being assembled;

FIG. 13 is a side elevational view of the set bone and showing in broken lines the spline completely assembled;

FIGS. 14 and 15 are side elevational views on an enlarged scale of the left and right, respectively, outer tubular members of a modified form of spline;

FIG. 16 is an end view of the left end of FIG. 14, being also substantially that of the right end of FIG. 15;

FIG. 17 is a sectional view on the line 17—17 of FIG. 14;

FIG. 18 is a sectional view on the line 18—18 of FIG. 14;

FIG. 19 is a fragmentary sectional view on the line 19—19 of FIG. 14;

FIG. 20 is a fragmentary side elevational view of the third central member of spline 34;

FIG. 21 is a longitudinal mid-sectional view of a fractured bone showing the modified spline partially applied; and FIG. 22 is another modified form of an outer tubular member.

DESCRIPTION OF THE PREFERRED EMBODIMENT

Referring to FIGS. 1–9, the three part spline pin 10 comprises the tubular outer members 11 and 12 shown, respectively, in FIGS. 1 and 2, and the central rod-like member 13 shown in FIG. 5. Members 11 and 12 each comprise a central tube-like portion 14 seen also in FIG. 7 with both ends threaded.

The distal end of each is provided with tap threads at 15L or 15R and the proximal end is provided with following or bone gripping threads at 16L or 16R. For the purposes of the description member 11 is referred to as the left hand member and designated 11L and member 12 is referred to as the right hand member and designated 12R. It will be understood that the members may be interchanged. The threads at 15L and 16L are shown as left-hand threads and the threads at 15R and 16R are shown as right-hand threads. When members 11 and 12 are secured in aligned relation, as will hereafter appear, the oppositely threaded members mutually resist rotation in an unthreading direction.

The tapping threads at 15 in both members are tapered and relieving grooves 17 are provided which may extend, at least in part, to the hollow center portion of the member, all as usual with such tap threads. The gripping threads 16 are of uniform diameter as shown, the tap threads being of such size as to provide thread grooves for the grip threads, as is usual.

Referring to FIGS. 5 and 6 the central or aligning rod 13 is square in cross section and is provided, on at least one side, with a series of holes or depressions 18 which are axially aligned and spaced therealong. For reasons of strength the holes 18 do not extend entirely through the rod 13 although in some cases they may. The length of rod 13 in most cases will be equal to the combined lengths of members 11 and 12 when placed end to end.

Referring now to FIGS. 3 and 4, the central space 19 of each of the tubular members 11 and 12 are reduced at each end by drawing to form passages 20 square in cross section providing a slide fit for the member 13. It will be understood that the FIGS. of the drawings are diagrammatical in the sense that the cross-sectional dimensions of rod 13 and passages 20 are shown smaller than necessity for clarity, particularly in FIGS. 10–13 which are reduced in scale.

Referring to FIGS. 8 and 9, means for locking the parts of pin 10 in place are provided, as will hereinafter be understood in connection with FIG. 13. As shown in FIG. 9 a hole 21, somewhat larger than the depressions 18, is provided in one end as shown of the rod 13. A detent ball 22 is provided in the hole, outwardly biased by a spring 23 and held in place by staking the bar 13 at 24,24 as shown. The ball 22 is adapted to be engaged in the socket hole 25 shown at the left in FIG. 1, it being understood that a similar socket hole may also be provided at the right in FIG. 2.

Referring now to FIGS. 10–13, the two portions 26L and 26R of an elongated bone 26, fractured at 27 are shown and the steps in installing and assembling the bone setting spline pin 10 are illustrated. In FIGS. 10 and 11 the bone portions are shown retracted from one another by known means and bent at an angle to one another to provide access to the intramedullary cavity 28 or bone channel at the fracture 27.

First, each bone portion is drilled at 30 to accommodate the distal or tap end of an outer tubular member and one bone portion is drilled on a lesser diameter at 31 to accommodate the insertion of the rod member 13 to the extent shown in FIG. 11. It will be understood that the angle of the drilling operation will depend on the skill of the surgeon and the extent of curvature of the bone 26 and its cavity 28. It is contemplated that a plurality of spline parts will be furnished, differing in outer diameter and in length so that the surgeon may make a selection according to the size of the intramedullary passage and the curvature thereof. Shorter outer tubular members may be furnished when the fracture is near one end of the bone, the outer members being not necessarily of the same length and various lengths of the central member 13 being supplied.

Second, the outer members 11L and 12R are threaded into place, the square passages 20 providing sockets for the insertion of rotating means for the outer members. The central member 13 is then inserted in one tubular member, the location of the socket hole 25 in the one or the other member 11 or 12 being duly considered.

Third, the bone portions 26L and 26R are then straightened into alignment, the spacing at the fracture 27 being maintained to some extent, as shown in FIG. 12. The central rod member 13 is then advanced to the left in FIG. 12 by inserting the pointed end of an instrument or pick into successive holes 18 in rod 13 at the break 27 and moving the rod to the left of FIG. 12 until the spring pressed ball 22 is received into the socket hole 25 of member 11L.

Fourth and finally, the retraction or traction device used to separate the bone portions 26L and 26R at the break at 27 is released and the bone ends are brought together by the natural muscular and sinew contractions in the affected limb, the pin 10 being completely assembled. From present observations the marrow matter removed by bores 30 and 31 soon is replaced by regrowth and the break at 27 is repaired by bone growth.

It will now be apparent that the intramedullary spline or pin 10 may be made as small as one-eighth inch in diameter or as large 1½ to 2 inches for use in bones of larger animals, such as the horse. The use of the pin 10 also has the following advantages over heretofore known devices: There is only one operative site and there is less trauma, less operative time and less risk of infection. There is less disruption of medullary bone and cellular architecture. There is less chance of future migration of the fixation device which should remain permanently in place. There is no axially projecting portion for further removal. There is no weakening of the cortical bone with transversely drilled holes and no need for surface application of bulky plates, screws or wires projecting into surrounding soft tissues. The choice of the size and length of the spline parts is optional with the surgeon, only dictated by circumstances and the type and location of the fracture. No part of the fixation device projects outside of the bone, no periosteal stripping being necessary and there is less interference with the development of cortical bone callus as with normal healing bones. The telescoping design of the device encourages impaction of the fracture site and bone to bone contact at the fracture site as bone absorption at the fracture site occurs with the first phase of normal healing. Weight bearing and normal muscle tone increase impaction and there is no further stress on the fixation device as with bone plates bridged across the fracture. Multiple size choice permits greatest choice of the rod length depending on the type of fracture and judgment of the surgeon.

Perhaps most importantly, the device provides rotatory or torsional stability of the bone portions, the threaded sleeves or outer portions of the device being secured in the intramedullary passage by self-tapping reverse threads, the sleeves being secured in the fracture ends of the bone and the square rod secured in the square passages of the sleeves. Rapid mobilization of the patient, within three days is expected, and with no need for cast or external splinting. Rotational or torsional stress control permits retaining the functional use of the extremity, as with bones which rotate with normal use, such as with fractures of the radius, without immobilization of adjacent joints, such as wrist and elbow.

As pointed out above, unequal portions of the spline in the bone portions is possible when the fracture is near either end of the bone. The device may also be used in communited or butterfly types of fracture to internally bridge the free fragment and provide stability at the fracture site.

Referring now to FIGS. 14, 15, 20 and 21, a modified form of spline 34 is shown, outer tubular members 35 and 36 and a central aligning rod 37. The principal difference in the members 35 and 36 from the similar members 11 and 12 of the spline 10 is in the type of threads used which may be termed continuous, sharp pointed spiral threads with uniform outer thread diameters rather than the more conventional graduated outer thread diameter of the tapping threads 15 with their relieving grooves 17.

The spline 34 is adapted to be used with fractured bones, such as bone 38 shown in FIG. 21, where the intramedullary canal 39 on either side of the fracture has a substantially equal diameter and is substantially aligned so that pre-boring is not required. As shown in FIGS. 14 and 15, the tapping threads 41 and the following threads 42 of each outer member are in continual spiral relationship and may be essentially the same. The starting edge 43 of each thread 41 is substantially radial of the outer member as shown in FIG. 16 whereas that of the following thread 42 may be more inclined, if desired. As shown in FIG. 21 only the outer pointed edge of the threads are in engagement with the bone cortex 44 around the canal 39.

The threads 41 and 42 of tubular member 35 are left-hand and those of member 36 are right-hand as shown in FIGS. 14 and 15. The passage through the central tubular portion 45 of each member is circular and the passage 46 at each end of each member has been drawn down to be square in cross section for a slide fit with the central rod member 37 which is square in cross section.

As best seen in FIGS. 16 and 19, the distal end of each member 35 and 36 has been provided with a substantially round, in cross section, enlargement or round groove 47 so that the central rod 37, which has a spring pressed ball 22 at one end, may be first inserted in either member 35 or 36 and without regard to which side the ball 22 projects.

Except for the omission of the initial boring operation, the installation of the spline 34 is the same as that described above for spline 10 as will be apparent from the description immediately hereabove.

Referring now to FIG. 22, a modified form of outer tubular member 49 is shown with threads 41 and groove 47 as described in connection with FIGS. 14 and 15 above. It will be apparent that, particularly with respect to smaller bones, the fracture may occur at a point near one end of the bone. In such a case the member 49 may be inserted in the intramedullary canal of the shorter bone portion, the length of member 49 being shorter than members 11, 12, 35 or 36. The smaller bones are usually those that do not carry as much weight as the larger bones such as those in the legs and hence the overall length of the spline need not be as great. As will be apparent, a central rod portion 37 of a shorter length must be chosen by the surgeon for use with the member 49.

We claim:

1. A three-part bone-setting spline pin for aligning and mutually non-rotatably securing together two portions of a fractured elongated bone, comprising: two tubular outer members adapted to be inserted through an incision at the point of fracture into the intramedullary passage in respective bone portions on either side of the fracture, each outer member having a plurality of radially projecting self tapping threads adapted to be screwed into gripping relation with the cortex of the bone portion around the intramedullary passage of a respective bone portion, and a third central rodlike aligning member of a length substantially equal to the length between the threads at the distal end of the one outer member and the threads at the distal end of the other outer member when the outer members are brought into end-to-end juxtaposition, the third member having a multisided cross-sectional shape, each outer member having for at least a portion of its length a reduced axial passage therethrough of a cross-sectional shape corresponding to that of the third member for containing therein the third member with a sliding fit, whereby the outer members are each screwed within the bony cortex of respective bone portions and then the third member inserted in the multisided passage of one outer member and then reciprocated into the passage of the other member when the bone portions are aligned.

2. A three part bone-setting spline pin for aligning and mutually non-rotatably securing together two portions of a fractured elongated bone, comprising: two tubular outer members adapted to be inserted through an incision at the point of fracture into the intramedullary passage in respective bone portions on either side of the fracture, each outer member having a plurality of radially projecting threads adapted to be screwed into gripping relation with the cortex of the bone portion around the intramedullary passage of a respective bone portion, the threads of one outer member being left-hand and the threads of the other outer member being right-hand, and a third central rod-like member substantially equal in length to the combined lengths of the outer members when placed in end-to-end juxtaposition, each outer member having at least at each end a reduced axial passage therethrough of a cross-sectional shape corresponding to the cross-sectional shape of the third member for containing therein the third member with a sliding fit; whereby the outer members are screwed within the bony cortex surrounding the intramedullary passage of its respective bone portion, the third member then inserted in the irregular shaped passages of the one member and into the intramedullary passage of the corresponding bone portion and then, after aligning the bone portions, reciprocated into the reduced passage of the outer member in the other bone portion.

3. The three-part bone-setting spline pin defined in claim 2 wherein the threads of each outer member are self-tapping and the threads of at least one outer member has tapping threads at its distal end thereof and has gripping threads at its proximal end spaced from the tapping threads, the said at least one outer member having at each end a reduced axial passage therethrough of a cross-sectional shape corresponding to the cross-sectional shape of the third member, the gripping threads being adapted to follow and enter into the thread grooves cut by the tapping threads; whereby the overall length of the spline pin is increased for the longer bones.

4. The spline pin defined in claim 2 wherein the cross-sectional shape of the third member and that of the reduced axial passages through the two outer members is square.

5. The spline pin defined in claim 2 wherein the third member has along at least one of its sides a plurality of spaced and aligned depressions, whereby a pointed instrument may be used to successively engage the depressions in the third member for moving it reciprocatively from the one outer member toward the aligned other outer member.

6. The spline pin defined in claim 2 wherein means for securing the third member in position after it has been reciprocated to within both aligned outer members comprises: an outwardly biased spring-pressed detent ball at at least one end of the third member, and a cooperating socket recess at the distal end of at least one outer member.

* * * * *